United States Patent
De Jonge et al.

(10) Patent No.: US 6,953,864 B2
(45) Date of Patent: Oct. 11, 2005

(54) METHOD FOR THE CATALYTIC CONVERSION OF ALKYLENE CARBONATE

(75) Inventors: Johannes Petrus De Jonge, Amsterdam (NL); Jean-Paul Lange, Amsterdam (NL); Dennis Humphrey Louis Pello, Amsterdam (NL)

(73) Assignee: Shell Oil Company, Houston, TX (US)

( * ) Notice: Subject to any disclaimer, the term of this patent is extended or adjusted under 35 U.S.C. 154(b) by 68 days.

(21) Appl. No.: 10/292,172

(22) Filed: Nov. 12, 2002

(65) Prior Publication Data

US 2003/0105366 A1 Jun. 5, 2003

(30) Foreign Application Priority Data

Nov. 13, 2001 (EP) .......................................... 01309560

(51) Int. Cl.$^7$ ............................................. C07C 69/96
(52) U.S. Cl. ..................................................... 558/277
(58) Field of Search ........................................ 558/277

(56) References Cited

U.S. PATENT DOCUMENTS

| | | | | |
|---|---|---|---|---|
| 4,582,645 A | * | 4/1986 | Spencer ..................... | 558/277 |
| 4,691,041 A | * | 9/1987 | Duranleau et al. .......... | 558/277 |
| 5,430,170 A | * | 7/1995 | Urano et al. ................ | 558/277 |
| 6,207,850 B1 | * | 3/2001 | Jiang et al. ................. | 558/277 |

FOREIGN PATENT DOCUMENTS

| | | | | |
|---|---|---|---|---|
| EP | 478073 | | 1/1992 | ........... C07B/41/08 |
| EP | 478075 | | 1/1992 | ........... C07B/37/06 |
| EP | 893428 | | 1/1999 | ........... C07C/68/06 |

OTHER PUBLICATIONS

Patent Abstracts of Japan, vol. 018, No. 619 (C–1278), Nov. 25, 1994 & Japan 06 238165 A (Nippon Shokubai Co. Ltd.), Aug. 30, 1994, abstract.

T. Tatsumi et al.: "Hydrotalcite–type materisl as catalysts for the synthesis of dimethyl carbonate from ethylene carbonate and methanol" Microporus and Mesoporous Materials, vol. 22, 1998, pp. 399–407, X0002196014 Elsevier Science Publishing, NY, US ISSN: 1387–1811.

H. Schaper et at.: "Stabilized Magnesia: a Novel Catalyst (Support) Material" Applied Catalysis, vol. 54, 1989, pp. 79–90.

* cited by examiner

*Primary Examiner*—Golam M M Shameem

(57) ABSTRACT

A method for catalytic conversion of alkylene carbonate, wherein alkylene carbonate is contacted with $C_1$–$C_5$ aliphatic alcohol and/or water in the presence of Mg, Al mixed (hydr) oxide catalyst having a Mg:Al molar ratio in the range of from 4 to 20.

4 Claims, No Drawings

METHOD FOR THE CATALYTIC CONVERSION OF ALKYLENE CARBONATE

This application claims the benefit of Application No. 01309560.9 filed on Nov. 13, 2001 in Europe under 35 U.S.C. § 119, § 365(a), or § 365(b).

1. Field of Invention

The present invention relates to a method for catalytic conversion of alkylene carbonate, using an Mg, Al mixed (hydr) oxide catalyst, and a catalyst therefore.

2. Background of the Invention

EP-A-0 51 351 disclose an Mg, Al mixed (hydr) oxide catalyst having an Mg: Al molar ratio above 3 and preferably in the range from 3–10.

The article of H. Schaper et al. in Applied Catalysis, 54, (1989) 79–90, discloses the same catalyst. This catalyst has a hydrotalcite structure, consisting of brucite type layers in which part of the bivalent ions (Mg) are replaced by trivalent ions, alternated by interlayers which contain water and anions to compensate for the excess charge of the trivalent ions. The preparation of such catalysts is disclosed. Due to the basic properties such catalysts are considered of special interest for base-catalyzed reactions, such as polymerization of propylene oxide, double-bond isomerisations of olefins such as 1-pentene, and aldol condensations. Exemplified is double-bond isomerisation of 1-pentene using an Mg, Al mixed oxide catalyst having an Mg:Al molar ratio of 5 and 10. At increasing molar ratio the conversion rate decreases.

The article of Watanabe, Y. et al. in Microporous and Mesoporous Materials 22 (1998) 399–407, discloses the use of Mg—Al hydrotalcite catalysts having a molar ratio of 1.8–2.5 for the methanolysis of ethylene carbonate for the production of dimethyl carbonate.

EP-A-0,478,073 describes a process for preparing a dialkyl carbonate which comprises contacting an alkylene carbonate with an alkanol in the presence of a mixed metal oxide catalyst or a modified bimetallic or polymetallic catalyst under conditions effective to produce the dialkyl carbonate. In the examples, a magnesium/aluminium mixed metal oxide catalyst having a Mg:Al ratio of 3:1 was employed.

In JP-A-06/238165, a process is described wherein an alkylene carbonate and an alcohol are subjected to transesterification in presence of a catalyst to produce a dialkyl carbonate. A combination of Magnesium oxide and another metal oxide other than magnesium was used as catalyst in an atomic ratio in the range of 1000:1 to 20:1 of magnesium to the other metal.

The present invention has for its object to provide a method for the catalytic conversion of alkylene carbonate having an improved conversion rate and improved yield, while having limited leaching of metal from the catalyst.

SUMMARY OF THE INVENTION

Accordingly, the invention provides a method for catalytic conversion of alkylene carbonate, wherein alkylene carbonate is contacted with $C_1$–$C_5$ aliphatic alcohol and/or water in the presence of Mg, Al mixed oxide catalyst having an Mg:Al molar ratio in the range of from 4 to 20.

DETAILED DESCRIPTION OF THE EMBODIMENTS

The invention is based on the insight that by increasing the Mg:Al molar ratio in this type of (hydrotalcite) catalyst conversion rate and yield both improve. Although in the preparation of the catalyst a so called mixed Mg/Al hydroxide is formed it might be that under working conditions mixed Mg/Al oxides also or only are present. The catalyst will be referred to as Mg, Al (hydr)oxide catalyst. At molar ratios above about 4, such as of from about 4 to about 20 Mg:Al and, preferably, above about 5 such as about 5 to about 20 the catalyst exhibits the highest activity.

During the catalytic conversion of alkylene carbonate metal oxide, in particular Mg, may leach from the catalyst particles. The leach rate is reduced when the Mg:Al molar ratio is below about 20, such as of from about 4 to about 20, preferably below about 10, such as of from about 4 to about 10. The MG,Al (hydr) oxide catalyst suitable for the purpose of the present invention will therefore have a Mg:Al ratio of at least about 4, preferably more than about 4, even more preferably at least about 5, and most preferably more than about 5. The Mg,Al (hydr) oxide catalyst will further preferably have a Mg:Al ratio of at most about 20, more preferably of less than about 20, even more preferably of at most about 15, again more preferably of less than about 15, most preferably of at most about 10.

Alkylene carbonate suitable for use in the catalytic conversion method according to the invention may be a $C_1$–$C_5$ alkylene carbonate such as 1,2 and 1,3 propylene carbonate, 1,2 and 2,3 butadiene carbonate. Preferred are ethylene carbonate and propylene carbonate. $C_1$–$C_5$ aliphatic alcohol suitable for use comprises a straight and branched $C_1$–$C_5$ alkanols. Preferred are methanol and ethanol. Most preferred is methanol. In the presence of one or a mixture of $C_1$–$C_5$ alkanol, the alcoholysis results in the formation of di($C_1$–$C_5$) alkyl carbonate and alkylene diol. In the presence of only methanol the methanolysis results in the formation of dimethyl carbonate and the alkylene diol. The catalytic conversion in the presence of only water results by hydrolysis in the production of the alkylene diol and carbon dioxide. The catalytic conversion in the presence of $C_1$–$C_5$ aliphatic alcohol and water results in the formation of all end products in ratio's dependent on the methanol:water molar ratio. When the molar ratio of methanol:water is higher than about 6, such as from about 10 to about 20. The dimethyl carbonate:alkylene diol molar ratio is between about 1 and about 0.

Another aspect of the invention relates to the use of this catalyst as defined above for the catalyst conversion of alkylene carbonate with $C_1$–$C_5$ aliphatic alcohol and/or water, and in particular to the methanolysis and/or hydrolysis of alkylene carbonate.

The Mg, Al mixed (hydr) oxide catalyst has generally a Mg:Al molar ratio in the range of of from about 4 to about 20. At higher molar ratio's leaching of the metal oxide, in particular Mg increases. For an optimal catalyst activity at low Mg leaching the Mg:Al molar ratio is in the range of from about 4 to about 20, in particular of from about 5 to about 10 or of from about 10 to about 20.

The method and use of the catalyst according to the invention will be further elucidated by reference to the following examples which are provided for illustrative purposes and to which the invention is not limited.

EXAMPLE 1

Catalyst Preparation

The Mg/Al samples were prepared by semi-batch co-precipitation at constant pH. Aqueous solutions of $Mg(NO_3)_2 \cdot 6H_2O$ (1 M) and $Al_2(SO_4)_3 \cdot 18H_2O$ (0.5 M) were prepared from demineralised water and mixed proportionally to the targeted Mg/Al molar ratio. The resulting solution was then added drop-wise to 600 ml of an aqueous solution of 25% $NH_3$ (pH=9) under constant stirring at 65° C. The precipitating solution was kept at pH=9 by addition of 25% $NH_3$ solution. The slurry was then aged for 1 hour under continuous stirring and filtered. The resulting paste was washed with demineralised-water until the pH of the wash water became neutral and, finally, dried over night at 80° C.

EXAMPLE 2

Catalyst Screening

The samples were evaluated in a unit equipped with 6 quartz reactors having an inner diameter of 3 mm. Catalyst charges of 0.15 gram (30–80 mesh size) were diluted with 0.45 gram of SiC (0.05 mm diameter) and loaded into the reactor, with a pre-bed of 0.45 gram SiC placed on top. The catalysts were dried in situ under $N_2$ flow at 120° C. for 1 hour. The reactors were then pressurised to 25–30 bar and the feed flow is started with a space velocity of WHSV=5 gr/(gr.hr), together with a moderate $N_2$ flow of WHSV=2 gr/(gr.hr). The liquid feed consisted of a PC:MeOH mixture of 1:4 molar ratio. After a stabilising period of 20 hours at 120° C., the liquid products were condensed at 15° C. and 1 bar during a 24 hours run for off-line GC analysis. The moderate $N_2$ flow needed for pressure regulation and product transport stripped some of the light ends from the sample. Therefore mass balances were only made on propylene carbonate.

In the following examples, the conversion of methanol and yield of dimethyl carbonate (DMC) are based on the molar amounts of these compounds divided by the molar amount of methanol supplied times 100%. The conversion of propylene carbonate to monopropyleneglycol (MPG) and/or methylpropanyl carbonate (MPC in mol %) and the yield of MPG and/or MPC are based on the molar amount of recovered PC divided by the molar amount of PC supplied in the feed times 100%.

TABLE 1 performance of Mg/Al (hydr) oxides for methanolysis of propene carbonate (120° C., total liquid WHSV = 5 g/g/h, a $N_2$ flow of WHSV of 2 g/g/h and 25 bar, catalyst calcined at 400° C. unless specified otherwise)

| Catalyst | Conv. MeOH[a] | PC[b] | Yield DMC[a] | MPG[b] | light ends[b] | MPC[b] |
|---|---|---|---|---|---|---|
| 1 Mg/Al[c] | 8.9 | 12.4 | 1.7 | 6.4 | 0.3 | 5.9 |
| 2 Mg/Al | 9.0 | 11.5 | 1.5 | 5.5 | 0.4 | 6.0 |
| 5 Mg/Al | 15.1 | 21.1 | 3.8 | 15.4 | 0.3 | 5.7 |
| 10 Mg/Al | 17.4 | 25.3 | 4.7 | 20.2 | 0.4 | 5.1 |
| 20 Mg/Al | 26.0 | 35.8 | 8.3 | 34.1 | 0.1 | 1.6 |
| 50 Mg/Al | 25.0 | 34.1 | 8.0 | 32.5 | 0.0 | 1.6 |
| Mg (OH)$_2$ | 6.6 | 8.6 | 1.8 | 7.0 | 0.0 | 1.6 |
| Effect of calcinations | | | | | | |
| 5 Mg/Al calc. 400° C. | 15.1 | 21.1 | 3.8 | 15.4 | 0.3 | 5.7 |
| 5 Mg/Al calc. 80° C. | 16.6 | 23.4 | 4.35 | 18.2 | 0.4 | 5.1 |
| 10 Mg/Al calc. 400° C. | 17.4 | 25.3 | 4.7 | 20.2 | 0.4 | 5.1 |
| 10 Mg/Al calc. 80° C. | 15.7 | 21.0 | 4.0 | 15.9 | 0.3 | 5.1 |

[a]dimethyl carbonate expressed in mole % based on methanol supplied in feed;
[b]monopropylene glycol and methyl propanyl carbonate (MPC) expressed in mole % based on propylene carbonate (PC) supplied in feed;
[c]xMG/Al implies a Mg:Al molar ratio of x.

According to table 1, the activity of the mixed Mg/Al (hydr) oxides increases with increasing Mg/Al ratio, exception made for the pure $Mg(OH)_2$ which shows one of the lowest activity, possibly because of leaching indicated by the formation of a hazy liquid product.

Calcining the materials at 80 or 400° C. prior to loading into the reactor had little influence on their catalytic performance. This illustrated for 5 Mg/Al and 10 Mg/Al in Table 1.

The 20 Mg/Al and 50 Mg/Al catalysts exhibit the highest activity, but degrade to some extent during the reaction such that the catalyst/SiC bed was very hard to remove from the reactor. By contrast, the other samples came out as free flowing particles. The $Mg(OH)_2$ sample was also free-flowing, though the haziness of the liquid product suggests significant leaching during the reaction.

Similar results have been obtained when using ethylene carbonate (EC) instead of propylene carbonate. Under the same operating conditions as applied for the examples of table 1, except for the ethylene carbonate which now substitutes the propylene carbonate in the feed, the 5 Mg/Al catalyst converted EC to EG with 28 mole % yield based on EC supplied in feed and a DMC/EG molar ratio of 0.89.

EXAMPLE 3

Catalyst Stability/Activity

In order to assess the stability of the various materials, samples of 0.1 g of each catalyst were immersed in 15 ml of a representative MeOH:PC:MPG mixture (3.46:0.88:0.24 molar ratio) for 20 hours at room temperature. Then 5 ml samples were taken from the top of the liquid and analysed with ICP-spectrometry. The magnesium content of these products increased with the Mg/Al molar ratio starting at Mg/Al of ~10 (Table 2). It is concluded that the 5 Mg/Al and 10 Mg/Al catalysts offer the best compromise between activity and stability in the reaction medium.

TABLE 2

Magnesium content of a MeOH:PC:MPG mixture (3.46:0.88:0.24 molar ratio) after 20 hours immersion of various Mg/Al mixed hydroxide at room temperature.

| Catalyst | Mg leaching [mg/kg] |
|---|---|
| 1 Mg/Al | 9.30 |
| 2 Mg/Al | 3.52 |
| 5 Mg/Al | 10.14 |
| 10 Mg/Al | 25.0 |
| 20 Mg/Al | 34.5 |
| 50 Mg/Al | 72.9 |
| Mg | 164.4 |

EXAMPLE 4

Performance in Methanolysis/Hydrolysis

The catalytic tests were carried out in a single-tube microflow unit which is equipped with a HPLC pump to feed the PC-MeOH-water mixture, a gas manifold to introduce $N_2$ at 0.7 Nl/h, a traced feed line, a stainless steel reactor of 15 mm ID (with thermowell) operating in down flow, a high-pressure condenser operating at room temperature and an automatic sampling manifold that distributes the liquid product sequentially over six bottle of 300 ml.

The reactor was typically charged with 2 g of catalyst (1.6 mm cylinders) diluted in 15 g of SiC. Once loaded, the reactor was heated up to reaction temperature (120–140° C.)

under a $N_2$ flow of 0.7 Nl/h (i.e. WHSV of ~0.4 g $N_2$/g cat/h) at 25–30 bar for 16 h. The reactor was then set to reaction temperature and pressure (25 bar), contacted with the partially vaporised feed at target velocity (typically 2 g liq./g cat/h) and operated under varying conditions for more than 1000 hours without interruption.

The liquid product was analysed off-line by means of GC using the polar column. The gas stream was not analysed. However, occasional use of a cold trap (−60° C.) in the gas line did not provide more than 0.05 C % (based on total feed) of additional product, which appeared to be mainly methanol upon immediate GC analysis.

TABLE 3 performance of 5 Mg/Al (hydr) oxide for methanolysis and/or hydrolysis of propene carbonate (140° C., total liquid WHSV = 2 g/g/h, a N2 flow of WHSV of 0.4 g/g/h and 25 bar)

| Feed MeOH: $H_2O$:PC | Conv. MeOH[a] | PC[b] | Yield DMC[a] | MPG[b] | light ends[b] | MPC[b] | DMC: MPG[c] |
|---|---|---|---|---|---|---|---|
| 4:0:1 | 22.6 | 39.7 | 8.7 | 34.1 | 0.7 | 2.3 | 1.0 |
| 1:0:1 | 22.8 | 11.6 | 10.6 | 10.0 | 0.3 | 1.4 | 1.1 |
| 0.5:0:1 | 28.1 | 6.3 | 12.6 | 5.4 | 0.3 | 0.6 | 1.1 |
| 4:0:1 | 22.6 | 39.7 | 8.2 | 34.1 | 0.7 | 2.3 | 1.0 |
| 3.8:0.2:1 | 7.4 | 36.3 | 3.5 | 35.0 | 0.1 | 1.3 | 0.4 |
| 3.4:0.6:1 | 1.4 | 52.2 | 0.5 | 50.8 | 0.0 | 1.4 | 0.0 |
| 0.5:0:1 | 28.1 | 6.3 | 12.6 | 5.4 | 0.3 | 0.6 | 1.1 |
| 0.3:0.2:1 | 2.4 | 21.1 | 0.5 | 20.6 | 0.0 | 0.4 | 0.0 |
| 0:0.36:1 | — | 35.1 | — | 35.1 | 0.0 | 0.0 | 0.0 |

[a]expressed in mole % based on methanol supplied in feed;
[b]expressed in mole % based on PC supplied in feed;
[c]expressed in mole:mole.

Table 3 shows that the 5 Mg/Al catalyst converts PC to MPG in the presence of methanol and/or water in varying ratio. The catalyst was stable for more than 1000 h and operated satisfactorily over a wide temperature range, from 120 to 180° C. and a variety of residence time, from 4 to 40 min (1/WHSV). By varying the feed composition it produced DMC/MPG in a ratio that varied from nearly 1:1 with a water-free feed to 0:1 with a methanol-free feed. The hydrolysis reaction turns out to proceed at higher rate than the methanolysis reaction (compare e.g. the feed of 0:0.36:1 with 0.5:0:1, respectively). In contrast to the hydrolysis reaction, the methanolysis is limited by thermodynamic equilibrium. These two phenomena result in a DMC:MPG molar ratio in the product that drops much faster than do the MeOH:$H_2O$ molar ratio in the feed. In other words, it suffices to substitute as small fraction of water for MeOH to uncouple the production of DMC from that of MPG.

The spent catalyst did not significantly differ from the fresh catalyst as characterised by XRD, XPS and bulk element analysis. The absence of significant chemical changes of 5 Mg/Al catalyst during the reaction of PC with MeOH is consistent with the low Mg and Al content (<10 ppm) of the liquid product measured by means of ICP analysis. When normalised to the production rate of MPG, the Mg leaching rate generally remained below 100 ppm (i.e. <100 mg Mg/kg MPG) and more typically <50 ppm. This low leaching rate holds for MeOH:PC as well as $H_2O$;PC and MeOH:$H_2O$:PC feeds.

Similar results are obtainable with other alkylene carbonates and $C_2$–$C_5$ aliphatic alcohols.

What is claimed is:

1. A process for producing di($C_1$–$C_5$) alkyl carbonate and alkylene diol, which process comprises the steps of contacting alkylene carbonate with $C_1$–$C_5$ aliphatic alcohol in the presence of a Mg, Al mixed (hydr) oxide catalyst having a Mg:Al molar ratio in the range of from about 4 to about 20.

2. A process for producing alkylene diol and carbon dioxide, which process comprises the steps of contacting alkylene carbonate with water in the presence of a Mg, Al mixed (hydr) oxide catalyst having a Mg:Al molar ratio in the range of from about 4 to about 20.

3. A product stream comprising di($C_1$–$C_5$) alkylcarbonate and alkylene diol made by a process comprising the steps of contacting alkylene carbonate with $C_1$–$C_5$ aliphatic alcohol in the presence of Mg, Al mixed (hydr) oxide catalyst having a Mg:Al molar ratio in the range of from about 4 to about 20.

4. A product stream comprising alkylene diol and carbon dioxide made by a process comprising the steps of contacting alkylene carbonate with water in the presence of a Mg, Al mixed (hydr) oxide catalyst having a Mg:Al molar ratio in the range of from about 4 to about 20.

* * * * *